United States Patent [19]

Steer et al.

[11] Patent Number: 5,662,629
[45] Date of Patent: Sep. 2, 1997

[54] OSTOMY COUPLING

[75] Inventors: Peter L. Steer, Sussex; Keith G. M. Hollands, Sompting; Graham Emery Steer, London; Ronald A. Plass, West Sussex; Howard Barratt, Surrey, all of England

[73] Assignee: E.R. Squibb & Sons, Inc., Princeton, N.J.

[21] Appl. No.: 631,460

[22] Filed: Apr. 12, 1996

[30] Foreign Application Priority Data

Apr. 13, 1995 [GB] United Kingdom .................. 9507666

[51] Int. Cl.$^6$ .................. A61F 5/44; B65D 45/30
[52] U.S. Cl. .................. 604/342; 604/338; 215/274; 215/279; 215/280
[58] Field of Search .................. 604/332, 338, 604/339, 342–344; 215/274, 275, 279, 280, 286

[56] References Cited

U.S. PATENT DOCUMENTS

| 1,840,021 | 1/1932 | Brooks | 215/275 |
| 5,364,379 | 11/1994 | Ozenne et al. | 604/344 |

FOREIGN PATENT DOCUMENTS

572378B1  12/1993  European Pat. Off. .............. 604/338

Primary Examiner—Robert A. Clarke
Attorney, Agent, or Firm—Stuart E. Krieger

[57] ABSTRACT

It would be desirable to have improved designs of ostomy couplings which embody a springy or resilient split ring as a locking ring.

In an ostomy coupling, first and second coupling members 20, 40 are held together by a springy flexible split locking ring 30. A plurality of tabs 31, 32, symmetrically arranged on each limb of the locking ring 30, can be withdrawn generally radially outwardly by movement of the locking ring to permit separation of the two coupling members. The ring 30 is generally circular in its unstressed condition.

5 Claims, 2 Drawing Sheets

OSTOMY COUPLING

BACKGROUND OF THE INVENTION

This invention relates to an ostomy coupling.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable commercial success is described and claimed in U.K. Patent No. 1,571, 657.

An ostomy coupling in which unlocking of two coupling parts is achieved by deforming a ring is disclosed in our U.K. Patent Application No. 9409037.0, which was filed 6 May 1994 but was published after the filing of this application.

In PCT Application WO91/01119, published 1991 and corresponding to European Patent 482 104B, there is disclosed a locking ring for an ostomy coupling. An ostomy coupling which embodies such a ring is shown in European Patent 572 378B. Features of this design are that inwardly sprung tongues on the ring peripherally surround the joined coupling parts and that a press-button engagement device as well as a hook and detent engagement device are included, apparently in a quest for secure retention of the locking ring on the coupling parts. It appears inevitable that quite intricate manipulation of this design of coupling is needed when applying or removing the bag.

It has been proposed by Kubo, in Japanese Utility Model No. 62-11610, published February 1985, that an ostomy device should have a double female ring structure which can interengage with a male ring. The male ring may be on the bag and the female ring on a skin-attachable adhesive pad, or vice-versa. The outer ring on the female ring is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts.

This arrangement, though perhaps operable in theory, has serious disadvantages in practice, for example (i) to connect or disconnect it is necessary to hold the coupling at four places, approximately spaced at 90° intervals around the periphery, (ii) pressing on two diametrically opposed regions will tend to bend the coupling out of its normal plane and the forces applied may easily cause the body side pad to be partially (or wholly) detached from the skin of the wearer, also the need to press in both ends of the diameter fully, and simultaneously, means that releasing the bag-side coupling is subject to uncertainty, (iii) the repeated attachment and withdrawal of the bag-side coupling part will cause the o-ring (provided to prevent escape of excreted matter between the male and female rings) to become worn, so compromising its sealing qualities with potentially highly embarrassing and undesirable results, (iv) the wearer may find it difficult to determine whether or not the two coupling parts are properly engaged, (v) the accuracy and forces needed for manipulation to connect or disconnect will be well beyond the capability of an infirm, confused, elderly or impatient wearer; (vi) it is hard to be sure that the appliance is properly locked; and (vii) in the case of large sizes, the old and infirm will find it physically difficult to span with their hand and push in diametrally opposed regions of the ring.

It is an aim of this invention to provide an improved design of ostomy couplings which is easily locked and unlocked by a non-dexterous person.

SUMMARY OF THE INVENTION

According to the present invention, there is provided an ostomy coupling in which first and second coupling members are held together by a springy flexible split locking ring and in which at least one tab is arranged on each limb of the locking ring, the tabs being symmetrically disposed, and in which the tabs can be withdrawn generally radially outwardly of the coupling by a downward movement of the locking ring to permit separation of the two coupling members.

According to a preferred embodiment of the invention, in its upper region the locking ring has a sinuous re-entrant portion, to the mid-region of which pressure can be applied to cause withdrawal of the tabs.

The movement of the locking ring which causes withdrawal of the tabs, may be achieved by a vertically downward push by a finger of a wearer of the coupling.

BRIEF DESCRIPTION OF THE DRAWINGS

The invention will be better understood from the following non-limiting description of an example thereof given with reference to the accompanying drawings in which.

DETAILED DESCRIPTION OF THE INVENTION

Referring to FIGS. 1–4, the ostomy coupling comprises first and second coupling members 20 and 40 and a split locking ring 30. The first coupling member 20 may be a plastics moulding and may be made of low or high density polyethylene. The second coupling member 40 may also be a plastics moulding, e.g. of EVA, LDPE or HDPE. In the preferred embodiment of the invention, the first coupling member 20 is the body-side member and the second coupling member 40 is the bag-side member. However, without departing from the invention, the first and second coupling members could be the bag-side and body-side respectively.

A medical grade adhesive pad is attached in any suitable way to the surface 20A of the first coupling member 20.

Figure 3A:
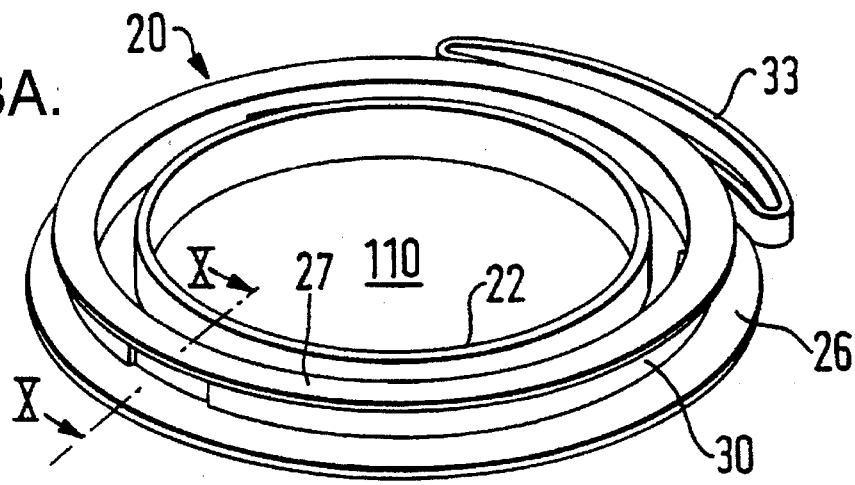
FIG. 3A is a similar view to FIG. 2 but shows all of the first coupling member, the ring being in place.
Figure 3B:
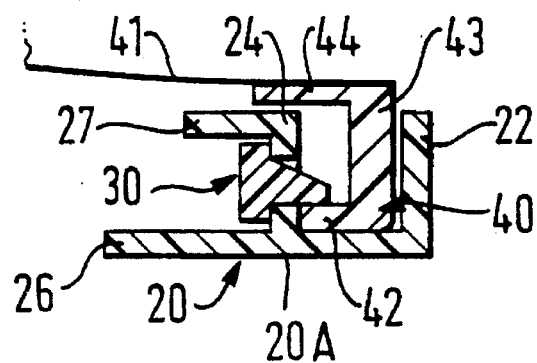
FIG. 3B is a cross-section at an end of a diamter and on a plane X—X of FIG. 3A which plane is perpendicular to the plane of the flange surface 20A of the first coupling member, and also showing the second coupling member.

The first coupling member 20 is best seen from FIGS. 3A and 3B and comprises a flange 26, an inner wall 22, an outer wall 24, and a cover flange 27. The lower surface as seen in FIG. 3B of the flange 26 normally has, in use, a medical grade adhesive pad adhered thereto in any suitable way. This adhesive pad secures the ostomy appliance to the body of the wearer, with the central stomal orifice 110 being capable of accommodating the stoma.

The second coupling member 40, which normally will be a bag-side coupling member, has a flange 42, FIG. 3B, which extends radially outwardly from a wall 43. An ostomy pouch wall 41 is attached to the second coupling member by any suitable means such as adhesive or heat or RF welding.

The remainder of the ostomy pouch is not shown, it being conventional. The stomal orifice is located to the right of wall 22 as seen in FIG. 3B.

Figure 1:
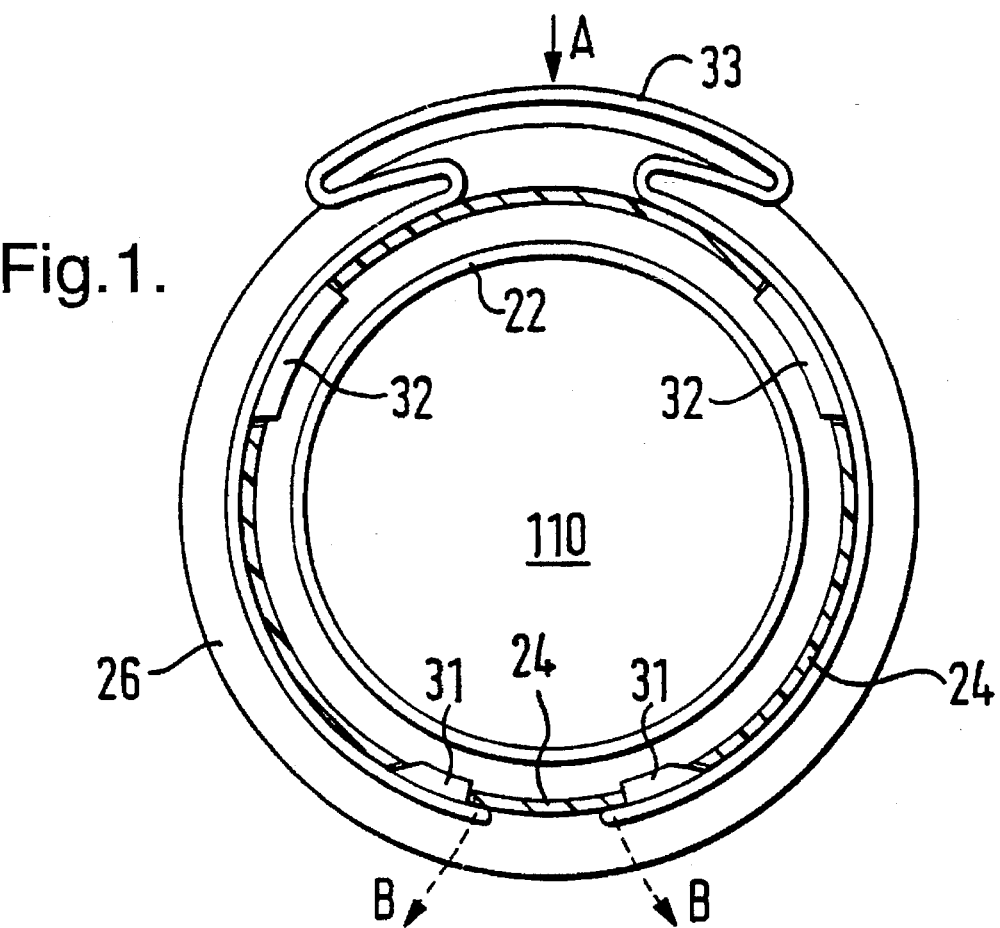
FIG. 1 is a plan view of a first embodiment of the invention, showing part of a first coupling member and a locking ring, the second coupling member not being shown.
Figure 2:
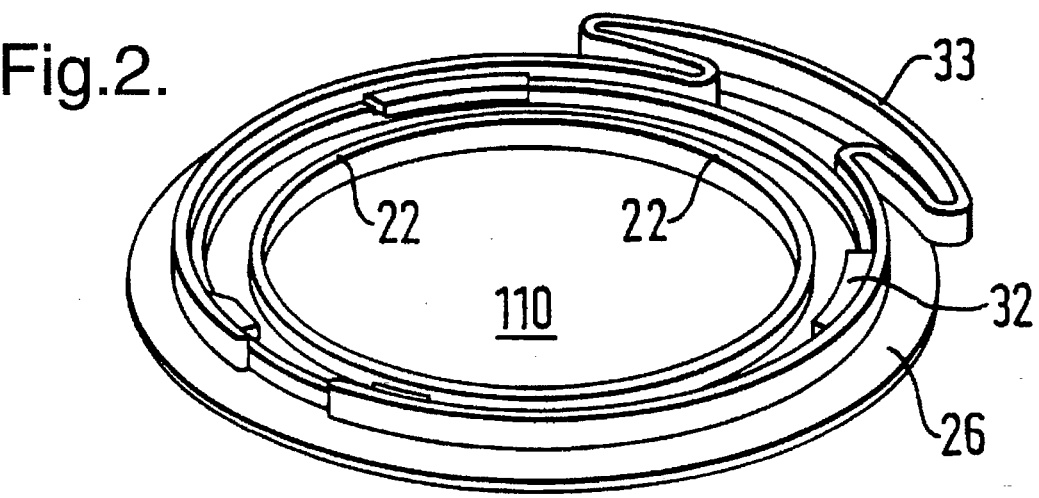
FIG. 2 is a perspective view showing the same parts as FIG. 1.
Figure 4:
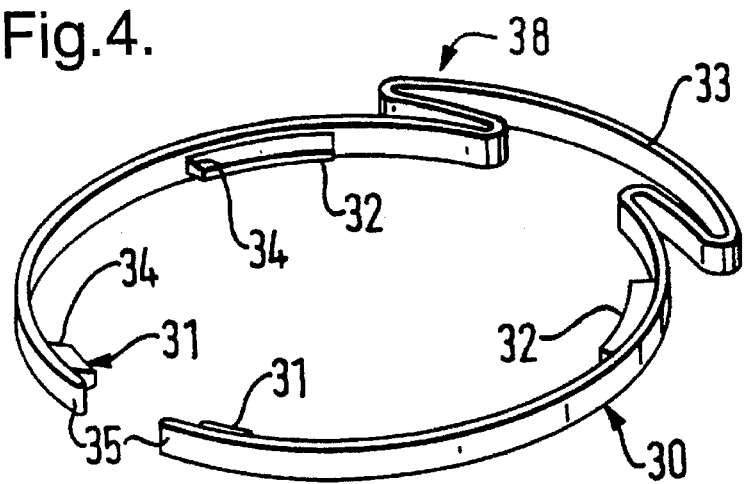
FIG. 4 is a perspective view of a locking ring for use in the invention.

The split locking ring 30 is best seen in FIG. 4, although it is also shown in FIGS. 1–3. It is made of a springy resilient plastics material such as acetal resin, and comprises two part-circular limbs whose free ends 35 respectively carry tabs 31, and other radially-inwardly extending tabs 32 are disposed at approximately two o'clock and ten o'clock, on the assumption that the ring and the coupling are in a normal upright position as they would be on the body of a wearer. The positions of these tabs may of course be varied. The shape of the ring 30 is seen best from FIGS. 1 and 4. It has a sinuous re-entrant portion 38, a part of which comprises a pressure portion 33. When a vertically downward force is applied to the centre of this portion 33, as indicated by the arrow A in FIG. 1, the ring is deformed so that the free ends 35 move outwardly as shown by the arrows B. This causes the tabs 31 to move outward, vacating the space between the walls 24 and 22 of the first coupling member, and freeing the flange 42 of the second coupling member. Once this flange is freed, the second coupling member and bag 41 attached thereto can be readily separated from the body side coupling member 20. For the material of the locking ring, good results have been achieved with an acetal copolymer known as 'KEMATAL' (Registered Trade Mark) which is also referred to as polyoxymethylene (POM) and is available from Hoechst. This is crystalline thermoplastic with an exceptionally stable polymer structure; a suitable grade is 'HOSTAFORM' (Registered Trade Mark) C. 27021.

The same pressure in the direction A results in the tabs 32 also moving generally radially outwardly, so likewise vacating the said space and freeing the flange 42 on the second coupling member 40 to move upwardly. By applying a light pulling pressure, in the direction of the axis of rotation of the coupling, which may be effected by gripping the periphery of the flange 44 through the thin material of the pouch and then gently pulling, the two coupling members can be separated. Only a light pulling force is needed, and if the ostomate uses the other hand to gently hold the first coupling member onto the skin, pain at the very tender peristomal area can be minimized.

As seen in FIG. 4, the upper surfaces of the tabs 31 and 32 are chamfered or radiused so as to provide a "lead in" guide when the wearer wishes to re-attach the bag-side coupling member with pouch attached thereto to the body-side coupling member 20. This chamfering 34 is also useful in the event that the tabs 32 are not completely withdrawn from the space between walls 22 and 24; if this is the case and the bag-side coupling member 40 is pushed directly towards the flange 26 of the body-side coupling member, the flange 42 pushes the tabs 31 and 32 radially outwardly during its travel. The upper flange 27 on the first coupling member serves to maintain the locking ring 30 within the coupling and prevents it being accidentally dislodged.

The second coupling member 40 is best seen in section in FIG. 3B and has a flange 44 to which one wall 41 of an ostomy pouch is attached. The member 40 has a second flange 42 which extends radially outwardly from an encircling wall 43. In use, the flange 42, in the locked condition of the coupling, is located between tabs 31 and 32 and the flange 26 of the first coupling member 20. When the tabs 31 and 32 are withdrawn approximately radially outwardly, as described above, then the first and second coupling members can be separated.

The medical grade adhesive pad previously referred to may comprise a base which is preferably a thin film of polymeric material such as polyethylene and an adhesive layer situated on the rear surface of a base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents.

It will be understood that modifications, alterations, and improvements could be made to the invention. For example, instead of having coupling members which are circular, it would be possible for them to be oval or of other closed loop shape. While the preferred material for the locking ring in each embodiment is an acetal resin, other plastics materials having the appropriate flexible and springy characteristics could be employed. Other mechanisms could be employed to disengage the tabs of the split locking ring from their locking positions. A flexible deflectible sealing strip may be provided on either the coupling member 20 or 40 to reduce the possibility of leakage and to take up any tolerances between the coupling members which may arise in manufacture.

What is claimed is:

1. An ostomy coupling comprising:

first and second coupling members capable of being coupled together, each of said members having a central stomal opening, said first coupling member having a flange with a projection receiving channel, said channel being defined at least in part by a concentric inner and outer wall, said inner wall being positioned closer to said stomal opening, said outer wall having a plurality of tab-receiving slots extending therethrough, said second coupling member having a projection receivable in said channel when said first and second members are properly pushed together, said projection being lockable in said channel, and a resilient, releasably lockable locking ring including a circular portion positionable circumferentially about said outer wall, said locking ring including a plurality of tabs projecting radially inwardly through said slots so as to lock said projection in said channel when said coupling members are coupled together, said locking ring including a compressible portion projecting radially outwardly from said circular portion, said compressible portion being compressible radially inwardly so as to move said circular portion of said locking ring radially outwardly and withdraw said tabs from said slots of said coupling member releasing said projection and facilitating uncoupling of said coupled members, said locking ring resiliently returning to lock said projection in said channel upon release of said compressible portion when said coupling members are coupled together.

2. The ostomy coupling as claimed in claim 1 wherein said tabs include a chamfered portion for guiding said tabs into said slots.

3. The ostomy coupling of claim 2 wherein said compressible portion is an extension offset from said circular portion.

4. The ostomy coupling of claim 3 wherein said extension is a partial loop.

5. The ostomy coupling of claim 2 wherein said locking ring includes two free ends.

* * * * *